United States Patent [19]

Schlegel et al.

[11] Patent Number: 4,496,590
[45] Date of Patent: Jan. 29, 1985

[54] BENZYL ALCOHOL DERIVATIVES, THEIR PREPARATION AND USE

[75] Inventors: Donald C. Schlegel, Schodack; Malcolm R. Bell, East Greenbush, both of N.Y.

[73] Assignee: Sterling Drug Inc., New York, N.Y.

[21] Appl. No.: 485,936

[22] Filed: Apr. 18, 1983

[51] Int. Cl.³ .................. A01N 33/02; A61K 31/335; C07C 50/10; C07C 97/10
[52] U.S. Cl. .............. 514/646; 260/396 N; 564/433; 514/826
[58] Field of Search .................. 260/396 N; 564/433; 424/330

[56] References Cited

U.S. PATENT DOCUMENTS 3,513,199  5/1970  Ross et al. ............................ 564/433
3,792,090  2/1974  Kalopissis et al. ............. 260/396 N
3,884,625  5/1975  Kalopissis et al. ............. 260/396 N
3,895,063  7/1975  Sallman et al. ...................... 260/570

FOREIGN PATENT DOCUMENTS 527794  10/1972  Switzerland ........................ 564/433
381217   8/1973  U.S.S.R. ............................. 564/433

OTHER PUBLICATIONS

Patai, The Chemistry of the Hydroxyl Group, part 2, 1971, pp. 1004, 1006.

I. Molnar and Th. Wagner-Jauregg, Helv. Chim. Acta 52, 401–408, (1969).

Primary Examiner—Glennon H. Hollrah
Assistant Examiner—Raymond Covington
Attorney, Agent, or Firm—Thomas L. Johnson; B. Woodrow Wyatt; Paul E. Dupont

[57] ABSTRACT

Novel hydroxyphenylaminobenzenealkanols, useful as antiasthmatic agents, are of the formula

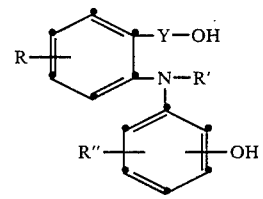

wherein R is hydrogen, lower-alkyl, lower-alkoxy or halo; R' is hydrogen or lower-alkyl; R" is hydrogen, lower-alkyl or halo; and Y is $C_nH_{2n}$ wherein n is 1–2. The compounds are prepared by de-etherification of the corresponding phenol alkyl or benzyl ethers; by reduction of the corresponding benzoic acids or esters thereof; or by reduction of ketones wherein —Y—OH is replaced by —COCH₃.

20 Claims, No Drawings

BENZYL ALCOHOL DERIVATIVES, THEIR PREPARATION AND USE

BACKGROUND OF THE INVENTION (1) Field of the Invention

The present invention relates to novel hydroxyphenylaminobenzenealkanols, their use as antiasthmatic agents, and processes for the preparation thereof.

(2) Information Disclosure Statement

I. Molnar and Th. Wagner-Jauregg, Helv. Chim. Acta 52, 401–408 (1969) disclose compounds of the following structure:

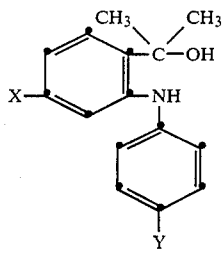

where X=H, Y=OCH$_3$; and X=CH$_3$O and Y=H, for use as intermediates in the preparation of antidepressant acridane compounds. The compound where X=CH$_3$O and Y=OCH$_2$C$_6$H$_5$ is also referred to, but the authors state that the compound could not be obtained.

A. Sallman and R. Pfister (Ciba-Geigy Corp.) U.S. Pat. No. 3,895,063, issued July 15, 1975, discloses compounds of the formula:

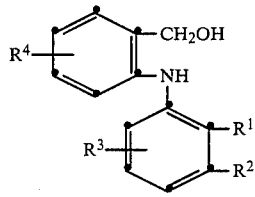

where:
R$^1$=lower-alkyl, lower-alkoxy, F, Cl
R$^2$=H, lower-alkyl, Cl, F
R$^3$=H, lower-alkyl, Cl, F
R$^4$=H, lower-alkyl, lower-alkoxy, Cl, F, Br.

The compounds are useful as intermediates in the preparation of anti-inflammatory agents.

SUMMARY OF THE INVENTION

In a product aspect, the invention relates to compounds of the formulas

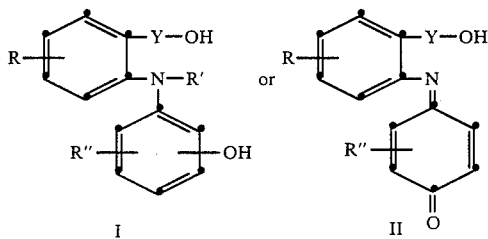

wherein:

R is hydrogen, lower-alkyl, lower-alkoxy or halo;
R' is hydrogen or lower-alkyl;
R" is hydrogen, lower-alkyl or halo; and
Y is C$_n$H$_{2n}$ wherein n is an integer from 1 to 2.

In a further product aspect, the invention relates to intermediates of the formula

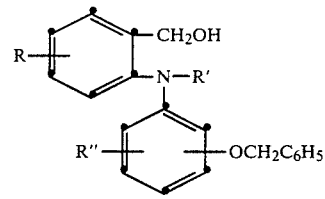

wherein:
R is hydrogen, lower-alkyl, lower-alkoxy or halo;
R' is hydrogen or lower-alkyl; and
R" is hydrogen, lower-alkyl or halo.

In a still further product aspect, the invention relates to compositions for the treatment or prevention of allergic asthma which comprise an anti-asthmatically effective amount of a compound of Formula I or II together with one or more pharmaceutically acceptable excipients or diluents.

In process aspects, the invention relates to a process for preparing a compound of Formula I which comprises a method selected from (a) subjecting a compound of the formula

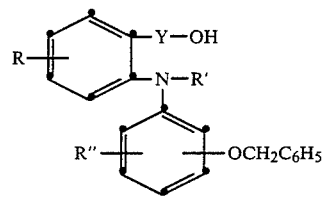

to catalytic hydrogenolysis;

(b) reducing a compound of the formula

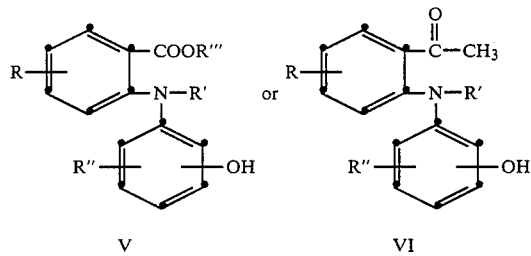

wherein R'" is hydrogen or lower-alkyl, with a metal hydride; and (c) treating a compound of the formula

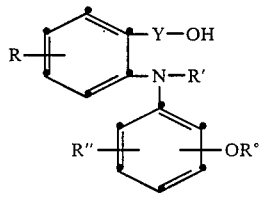

wherein R° is lower-alkyl and R is other than lower-alkoxy with a strong protonic acid or a Lewis acid.

In a further process aspect, the invention relates to a process for preparing a compound of Formula II which comprises reacting a compound of Formula I where R' is hydrogen:

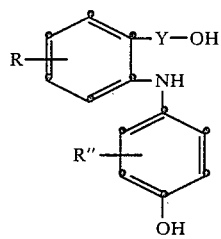

with an oxidizing agent capable of converting para-aminophenols to the corresponding 4-imino-2,5-cyclohexadien-1-ones.

In a still further process aspect, the invention relates to a method for treating or preventing allergic asthma in a mammal which comprises administering to said mammal a composition comprising an anti-asthmatically effective amount of a compound of Formula I or II together with one or more pharmaceutically acceptable excipients or diluents.

DETAILED DESCRIPTION INCLUSIVE OF PREFERRED EMBODIMENTS

In the foregoing Formulas I through VII, the variables R, R', R" and R''' when they stand for lower-alkyl or lower-alkoxy include such groups containing from one to three carbon atoms; and when R or R" stands for halo, it can be any of the common halogens, fluorine, chlorine, bromine or iodine. The variable Y, defined as $C_nH_{2n}$ where n is 1 or 2, includes methylene (—CH$_2$—), ethylene (—CH$_2$CH$_2$—) and methylmethylene [—CH(CH$_3$)—].

The synthetic approach to the compounds of Formula I is outlined in the following flow sheet:

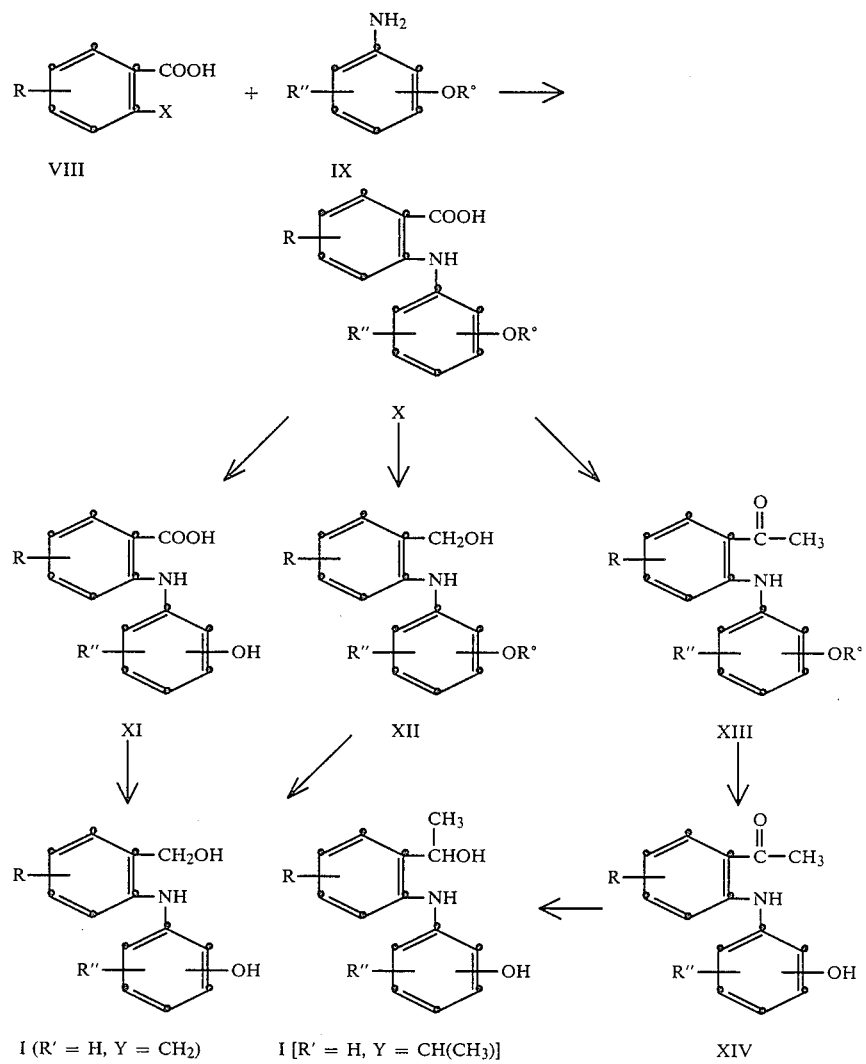

A 2-halobenzoic acid (VIII, where X is Cl, Br or I) is caused to react with an aminophenol ether (IX, where R° is benzyl or lower-alkyl), usually in the presence of a catalyst such as cupric acetate, to yield an anthranilic acid derivative of Formula X.

The Formula X structure can be converted to the corresponding phenol (XI) by dealkylation with a protonic or Lewis acid or debenzylation by catalytic hydrogenation. Reduction of the phenolic acid (XI) with a metal hydride gives a compound of Formula I where R''=H and Y=CH$_2$. The reduction takes place readily in an inert solvent under anhydrous conditions at ambient temperatures.

Alternatively, a compound of Formula X can be reduced with a metal hydride to give a compound of Formula XII, which by dealkylation or debenzylation gives a compound of Formula I where R'=H and Y=CH$_2$.

The same results can also be obtained starting with a lower-alkyl ester of X, which can be de-etherified to a lower-alkyl ester of XI and the latter reduced with a metal hydride to a compound of Formula I; or said lower-alkyl ester of X can be reduced with a metal hydride to a compound of Formula XII.

The compounds of Formula I where R'=H and Y=CH(CH$_3$) are prepared as follows: An acid of Formula X is caused to react with methyllithium to produce a methyl ketone of Formula XIII. The latter is then dealkylated or debenzylated to the phenolic ketone (XIV) which is then reduced with a metal hydride to the corresponding alcohol (I; R'=H, Y=CH(CH$_3$)). The reduction and de-etherification steps can if desired be reversed.

The compounds of Formula I where Y=CH$_2$CH$_2$ can be prepared from intermediates in the above flow sheet as follows: An acid of Formula X is subjected to an Arndt-Eistert homologation reaction to form the corresponding acetic acid derivative:

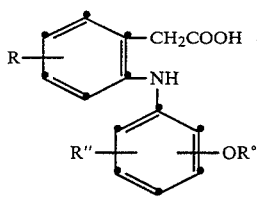

XV

The latter is then de-etherified and reduced with a metal hydride to produce a compound of the formula

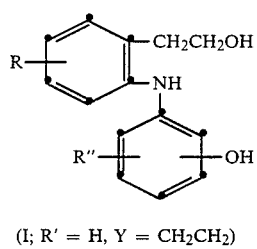

(I; R' = H, Y = CH$_2$CH$_2$)

Alternatively the acetic acid derivative of Formula XV can be produced from the methanol derivative of Formula XII by conventional procedures involving successive conversion of the methanol group (CH$_2$OH) to chloromethyl (CH$_2$Cl) and thence to cyanomethyl (CH$_2$CN) which can be hydrolyzed to carboxymethyl (CH$_2$COOH).

The N-lower-alkyl group (R'=lower-alkyl) in compounds of Formula I can be introduced at any intermediate stage where the phenolic hydroxy group is protected as an ether (R°). The alkylation is effected with a lower-alkyl halid (preferably bromide or iodide) in the presence of a strong base.

The compounds of Formula II are formed by oxidation of compounds of Formula I where R'=H and the hydroxy group is in the para-position with respect to the nitrogen. The oxidation takes place readily in the presence of oxidizing agents known to convert para-aminophenols to the corresponding 4-imino-2,5-cyclohexadien-1-ones. Such oxidizing agents include elementary oxygen, hydrogen peroxide, organic peroxides and various salts in a highly oxidized state such as perchlorates and periodates. In fact, solutions of compounds of Formula I where R'=H, and OH is in the para-position unless protected from contact with air have a tendency to be converted in part to the corresponding compounds of Formula II.

The following examples will further illustrate the invention.

Example 1

(a) 2-(4-Benzyloxyphenylamino)-5-methoxybenzoic acid [X; R=5—CH$_3$O, OR°=4—OCH$_2$C$_6$H$_5$, R''=H].

A mixture of 231 g of 2-bromo-5-methoxybenzoic acid, 262 g of 4-benzyloxyaniline hydrochloride, 160 g of potassium carbonate and 2 g of activated copper powder in about 2100 ml of amyl alcohol was heated at reflux with stirring for 4.5 hours. The reaction mixture was concentrated in vacuo and the residue dissolved in 6 liters of water. The solution was filtered and acidified with hydrochloric acid. The solid which formed was collected and recrystallized twice from benzene-cyclohexane to give 245 g of 2-(4-benzyloxyphenylamino)-5-methoxybenzoic acid, m.p. 167°–168° C.

(b) 2-(4-Benzyloxyphenylamino)-5-methoxybenzenemethanol [III; R=5—CH$_3$O, R' and R''=H, OCH$_2$C$_6$H$_5$ at 4-position].

To a stirred suspension of 10 g of lithium aluminum hydride in 1 in liter dry ether under nitrogen was added over a period of one hour a solution of 35 g of 2-(4-benzyloxyphenylamino)-5-methoxybenzoic acid in 300 ml of tetrahydrofuran. The mixture was heated at reflux for three hours, then cooled, and water (20 ml) was slowly added. The solid material was removed by filtration and the filtrate concentrated in vacuo. The residue was crystallized and recrystallized from a benzene-cyclohexane-hexane mixture to yield 26 g of 2-(4-benzyloxyphenylamino)-5-methoxybenzenemethanol, light tan crystals, m.p. 100°–101° C.

(c) 2-(4-Hydroxyphenylamino)-5-methoxybenzenemethanol [I; R=5—CH$_3$O, R' and R''=H, Y=CH$_2$, OH at 4-position].

To a solution of 2.41 g of 2-(4-benzyloxyphenylamino)-5-methoxybenzenemethanol in 200 ml of ethanol was added 60 mg of 10% palladium-on-carbon catalyst, and the mixture was hydrogenated on a Parr apparatus at room temperature and an initial pressure of 34 psi for 73 minutes. The reaction mixture was filtered and concentrated in vacuo to a volume of about 10 ml. Toluene (40 ml) was added and about half of the volume evaporated. The solution was cooled and crystallization induced. The solid product was collected and dried to give 1.3 g of 2-(4-hydroxyphenylamino)-5-methoxybenzenemethanol, pale lavender powder, m.p. 96.5°–97° C.

EXAMPLE 1A (a) 2-(4-Benzyloxyphenylamino)-5-methoxybenzoic acid.

To a 5 L 3-neck flask was added 282 g (2.06 moles) milled potassium carbonate and 1.0 L dimethylformamide. While stirring the resulting mixture at room temperature, 250 g (1.06 moles) 4-benzyloxyaniline hydrochloride was added portionwise over 15 minutes. After this was completed, 231 g (1.0 mole) 2-bromo-5-methoxybenzoic acid was added over 15 minutes and the mixture was stirred for another 15 minutes. The suspension was cooled to 10°–15° C. and 13.8 g cupric acetate monohydrate (0.06 moles) was added portionwise over 20 minutes. Gas evolved slowly and after stirring 15 minutes at room temperature the reaction was warmed on a steam bath over 40 minutes to 70° C. whereupon a vigorous evolution of carbon dioxide was observed. Stirring and heating was continued for 90 minutes at 80°–85° C., heat was removed and the mixture was allowed to cool to room temperature. The brownish red suspension was transferred to a 12 L flask containing 1 L ice-cold water. Acetic acid (650 ml) was added dropwise and the dark green precipitate was stirred vigorously until homogenous. After filtering and washing well with water, the crude product was dried overnight at 55°–60° C. in a vacuum oven. The crude product (approximately 350 g) was diluted with 5.8 L toluene, heated to reflux temperature and filtered. The dark green filtrate was alowed to cool to room temperature for 2–3 hours, and the solid product was collected by filtration and rinsed with cold (5°–10° C.) toluene. The bright yellow crystalline product was obtained in 80% yield.

(b) 2-(4-Benzyloxyphenylamino)-5-methoxybenzenemethanol.

To a 12 L flask containing 700 ml toluene was added 670 ml (2.31 moles) Red Al [sodium bis(2-methoxyethoxy)aluminum hydride - 3.4 moles in toluene]. A solution containing 300 g (0.859 moles) of 2-(4-benzyloxyphenylamino)-5-methoxybenzoic acid in 1.1 L tetrahydrofuran and 1.8 L toluene was added dropwise under $N_2$ at room temperature over a $3\frac{1}{2}$ hour period. The reduction was mildly exothermic, but the temperature did not exceed 35° C. Stirring was continued for another 30 minutes and then the solution was cooled to 20° C. A solution of 30% Rochelle salts (1.2 L) was added dropwise and the layers were separated. The organic layer was washed with brine, dried over magnesium sulfate, and the solvent was evaporated under vacuum. The crude product was crystallized from 600 ml isopropyl alcohol upon cooling to 0° C. After filtration the cake was washed three times with a small volume of cold isopropyl alcohol and then dried under vacuum at room temperature. The yield was 278 g (96.5%) of 2-(4-benzyloxyphenylamino)-5-methoxybenzenemethanol.

(c) 2-(4-Hydroxyphenylamino)-5-methoxybenzenemethanol.

2-(4-Benzyloxyphenylamino)-5-methoxybenzenemethanol (120 g, 0.357 mole) was diluted with 1.2 L ethyl acetate and 5.0 g 10% Pd/C catalyst was added under $N_2$. The suspension was reduced on a Parr apparatus over a $3\frac{1}{2}$–4 hour period. The suspension was filtered under $N_2$ usng an in-line filter, the filter rinsed well with ethyl acetate, and the clear solution was evaporated to dryness on rotary evaporator. The tan crystalline residue was then diluted with 60 ml ethyl acetate and 600 ml toluene. The suspension was heated on a steam bath to 75° C. After seeding and stirring, the product crystallized upon cooling slowly ($1\frac{1}{2}$ hours). Later, when room temperature had been reached, it was cooled further in an ice bath (4° C.) for 3 hours. The product was collected by filtration, and the filter cake was washed twice with an ice cold mixture of 1 part ethyl acetate-2 parts toluene, followed by a final rinse with hexane. The gray crystalline product was dried overnight in a vacuum oven at 50° C. and a 91% yield of pure product with m.p. 97°–98° C. was obtained. An X-ray examination of the crystalline structure showed that the product was a polymorphic form of the compound obtained in Example 1, part (c).

EXAMPLE 2

(a) 2-(4-Benzyloxyphenylamino)benzoic acid [X; R=H, OR°=4-OCH$_2$C$_6$H$_5$, R''=H] was prepared from 2-chlorobenzoic acid and 4-benzyloxyaniline hydrochloride according to the procedure of Example 1A, part (a), and the crude product was used directly in the following reaction.

(b) 2-(4-Benzyloxyphenylamino)benzenemethanol [III; R, R' and R''=H, OCH$_2$C$_6$H$_5$ at 4-position] was prepared by reduction of 2-(4-benzyloxyphenylamino)-benzoic acid with lithium aluminum hydride according to the procedure of Example 1, part (b), and was obtained in the form of a gray powder, m.p. 97°–98° C. when recrystallized from acetonitrile.

(c) 2-(4-Hydroxyphenylamino)benzenemethanol [I; R, R' and R''=H, Y=CH$_2$, OH at 4-position] was prepared by hydrogenation of 2-(4-benzyloxyphenylamino)benzenemethanol according to the procedure of Example 1, part (c), and was obtained in the form of a tan powder, m.p. 109°–111° C. when recrystallized from methylene dichloride.

In this reaction the crude product was a mixture of 2-(4-hydroxyphenylamino)benzenemethanol and 4-(2-methylphenylamino)phenol, m.p. 88°–89° C. The two compounds were separated by chromatography.

EXAMPLE 3

(a) 5-Chloro-2-(4-methoxyphenylamino)benzoic acid [X; R=5-Cl, OR°=4-OCH$_3$, R''=H] was prepared from 2,5-dichlorobenzoic acid and p-methoxyaniline according to the procedure of Example 1A, part (a), and obtained as a light green solid, m.p. 188°–189° C.

(b) 5-Chloro-2-(4-hydroxyphenylamino)benzoic acid [XI; R=5-Cl, R''=H, OH at 4-position].

Boron tribromide (250 ml, 0.8 molar) in methylene dichloride was added dropwise over a period of 70 minutes to a mixture of 25.1 g of 5-chloro-2-(4-methoxyphenylamino)benzoic acid and 125 ml of dry methylene dichloride cooled to −70° C. (Dry Ice/methylene dichloride). The cooling bath was removed and the reaction mixture stirred for about 20 hours. The volatile solvent was stripped off and water (400 ml) was added dropwise to the residue cooled in an ice bath. The mixture was then made basic by addition of potassium carbonate and then acidified with dropwise addition of hydrochloric acid. The solid was collected by filtration and dried to give 19.3 g of 5-chloro-2-(4-hydroxyphenylamino)benzoic acid.

(c) 5-Chloro-2-(4-hydroxyphenylamino)benzenemethanol [I; R=5-Cl, R' and R''=H, Y=CH$_2$, OH at 4-position] was prepared by reduction of 5-chloro-2-(4-hydroxyphenylamino)benzoic acid with lithium aluminum hydride according to the procedure of Example 1, part (b), and was obtained in the form of a pinkish-brown powder, m.p. 130°–131° C.

Alternatively, 5-chloro-2-(4-hydroxyphenylamino)-benzenemethanol can be prepared by hydrogenolysis of 5-chloro-2-(4-benzyloxyphenylamino)benzenemethanol, m.p. 73°–76° C., which was prepared by lithium aluminum hydride reduction of 5-chloro-2-(4-benzyloxyphenylamino)benzoic acid, in turn prepared by reaction of 2,5-dichlorobenzoic acid and 4-benzyloxyaniline.

EXAMPLE 4

(a) 4-Chloro-2-(4-methoxyphenylamino)benzoic acid [X; R=4-Cl, OR°=4-OCH$_3$, R''=H] was prepared from 2,4-dichlorobenzoic acid and p-methoxyaniline according to the procedure of Example 1A, part (a), and was obtained as a green-gray solid used directly in the following reaction.

(b) 4-Chloro-2-(4-hydroxyphenylamino)benzoic acid [XI; R=4Cl, R''=H, OH at 4-position] was prepared by reaction of 4-chloro-2-(4-methoxyphenylamino)benzoic acid with boron tribromide according to the procedure of Example 3, part (b), and obtained as a gray solid, m.p. 164°-165° C.

(c) 4-Chloro-2-(4-hydroxyphenylamino)benzenemethanol [I; R=4-Cl, R' and R''=H, Y=CH$_2$, OH at 4-position] was prepared by reduction of 4-chloro-2-(4-hydroxyphenylamino)benzoic acid with lithium aluminum hydride according to the procedure of Example 1, part (b), and obtained in the form of a grayish-pink powder, m.p. 126°-127° C. when recrystallized from methylene dichloride.

EXAMPLE 5

(a) 1-[2-(4-Benzyloxyphenylamino)phenyl]ethanone [XIII; R=H, OR°=4-OCH$_2$C$_6$H$_5$, R''=H].

Methyllithium (280 ml, 1M in ether) was added slowly to a solution of 31.9 g (0.1 mole) of 2-(4-benzyloxyphenylamino)benzoic acid (Example 2, part a) in 300 ml of tetrahydrofuran cooled to 0°-5° C. The reaction mixture was stirred at 0°-5° C. for 75 minutes. Ethyl acetate was then added and the mixture poured into a mixture of ice and saturated ammonium chloride solution. The aqueous suspension was extracted with ether, the ether extracts dried over anhydrous magnesium sulfate and concentrated. The residue was recrystallized from isopropyl alcohol to give 24 g of 1-[2-(4-benzyloxyphenylamino)phenyl]ethanone.

(b) 1-[2-(4-Hydroxyphenylamino)phenyl]ethanone [XIV; R and R''=H, OH at 4-position].

1-[2-(4-Benzyloxphenylamino)phenyl]ethanone (9 g) in 900 ml of ethanol and 90 ml of acetic acid was hydrogenated in the presence of 1 g of 10% palladium-on-carbon catalyst. There was obtained 3.6 g of 1-[2-(4-hydroxyphenylamino)phenyl]ethanone, orange solid, m.p. 168°-169° C.

(c) 2-(4-Hydroxyphenylamino)-α-methylbenzenemethanol [I; R, R' and R''=H, Y=CH(CH$_3$), OH at 4-position].

Sodium borohydride (630 mg) was added to a solution of 4.6 g of 1-[2-(4-hydroxyphenylamino)phenyl]ethanone in 80 ml of ethanol cooled to 10° C. and the mixture was stirred for 45 minutes. An additional 630 mg of sodium borohydride was then added and the reaction mixture stirred for an additional 90 minutes. The reaction mixture was poured into ice-water, treated with saturated sodium chloride solution and extracted with ether. The ether extract was washed with water, dried over anhydrous magnesium sulfate and concentrated. The residue was subjected to high pressure liquid chromatography using 20% acetone-80% hexane as a solvent system. Later fractions brought out the desired product, 2-(4-hydroxyphenylamino)-α-methylbenzenemethanol in the form of a brown solid, m.p. 30°-32° C.

EXAMPLE 6

(a) 1-[2-(4-Benzyloxyphenylamino)-5-methoxyphenyl]ethanone [XIII; R=5-CH$_3$O, OR°=4-OCH$_2$C$_6$H$_5$, R''=H] was prepared by reduction of 2-(4-benzyloxyphenylamino)-5-methoxybenzoic acid (Example 1A, part a) with methyllithium according to the procedure of Example 5, part (a), and obtained in the form of a yellow-orange powder, m.p. 80°-81.5° C. when recrystallized from toluene.

(b) 1-[2-(4-Hydroxyphenylamino)-5-methoxyphenyl]ethanone [XIV; R=5-CH$_3$O, R''=H, OH at 4-position] was prepared by hydrogenation of 1-[2-(4-benzyloxyphenylamino)-5-methoxyphenyl]ethanone according to the procedure of Example 5, part (b), and obtained in the form of an orange powder, m.p. 118°-119° C. after chromatography on silica gel with chloroform eluant.

(c) 2-(4-Hydroxyphenylamino)-5-methoxy-α-methylbenzenemethanol [I; R=5-CH$_3$O, R' and R''=H, Y=CH(CH$_3$), OH at 4-position] was prepared by reductionof 1-[2-(4-hydroxyphenylamino)-5-methoxyphenyl]ethanone with sodium borohydride according to the procedure of Example 5, part (c), and obtained in the form of an off-white to gray powder, m.p. 115°-116° C.

EXAMPLE 7

(a) Methyl 2-[methyl(4-benzyloxyphenyl)amino]benzoate.

2-(4-Benzyloxyphenylamino)benzoic acid (30.0 g, 0.094 mole) was added portionwise to a stirred suspension of sodium hydride (0.376 mole, from 18.0 g of 50% oil suspension washed with pentane) in 300 ml of dimethylformamide cooled in an ice-bath. The ice-bath was removed and the reaction mixture stirred for 35 minutes. The ice-bath was then replaced and 23.4 ml of methyl iodide added dropwise over 12 minutes. After stirring the mixture for one hour at room temperature, it was again cooled and an additional 12 ml of methyl iodide added. The reaction mixture was stirred for about 16 hours, then poured into ice-water and extracted with ethyl acetate. The extract was dried over magnesium sulfate and concentrated to an oil which crystallized (35.8 g). The latter, comprising a mixture of methyl 2-(4-benzyloxyphenylamino)benzoate and its N-methyl derivative, was chromatographed on silica and the major factions recrystallized from isopropyl alcohol to give said N-methyl derivative, 25.3 g, m.p. 57°-59° C.

(b) 2-[Methyl(4-benzyloxyphenyl)amino]benzenemethanol ]III; R and R''=H, R'=CH$_3$, OCH$_2$C$_6$H$_5$ at 4-position] was prepared by reduction of methyl 2-[methyl(4-benzyloxyphenyl)amino]benzoate with lithium aluminum hydride according to the procedure of Example 1, part (b), and was obtained in the form of colorless prisms, m.p. 89°-90° C.

2-[Methyl(4-benzyloxyphenyl)amino]benzenemethanol can be hydrogenated according to the procedure of Exmple 1A, part (c) to produce 2-[methyl(4-hydroxyphenyl)amino]benzenemethanol [I; R and R''=H, R'=CH$_3$, Y=CH$_2$, OH at 4-position].

EXAMPLE 8

4-(2-Hydroxymethyl-4-methoxyphenylimino)-2,5-cyclohexadien-1-one [II; R=4-CH$_3$O, Y=CH$_2$, R''=H].

To a suspension of 3.7 g of 2-(4-hydroxyphenylamino)-5- methoxybenzenemethanol (Example 1c) in 300 ml of methylene dichloride was added 32 g of silica treated sodium metaperiodate. The reaction mixture was stirred for two hours at room temperature, then filtered and washed with water and dried over anhydrous sodium sulfate. The solution was concentrated and the residue triturated with hexane to give 1.1 g of 4-(2-hydroxymethyl-4-methoxyphenylimino)-2,5-cyclohexadien-1-one, m.p. 87°–89° C.

EXAMPLE 9

(a) 2-(3-Chloro-4-hydroxyphenylamino)benzoic acid [XI; R=H, R''=3-Cl, OH at 4-position] was prepared by reaction of 2-(3-chloro-4-methoxyphenylamino)benzoic acid (prepared from 3-chloroanisidine and 2-chlorobenzoic acid) with boron tribromide according to the procedure of Example 3, part (b), and was obtained as a pale yellow powder, m.p. 180°–183° C. (decompn.).

(b) 2-(3-Chloro-4-hydroxyphenylamino)benzenemethanol [I; R and R'=H, R''=3Cl, Y=CH$_2$, OH at 4-position] was prepared by reduction of 2-(3-chloro-4-hydroxyphenylamino)benzoic acid with lithium aluminum hydride according to the procedure of Example 1, part (b), and was obtained as a solid, m.p. 107°–108° C. when recrystallized from aqueous ethanol.

EXAMPLE 10

(a) Ethyl 2-(2-hydroxyphenylamino)benzoate, m.p. 105°–106° C., was prepared by boron tribromide demethylation of ethyl 2-(2-methoxyphenylamino)benzoate. The latter was prepared by esterification of 2-(2-methoxyphenylamino)benzoic acid, in turn prepared by reaction of 2-chlorobenzoic acid with 2-methoxyaniline.

(b) It is contemplated that 2-(2-hydroxyphenylamino)benzenemethanol [I; R, R' and R''=H, Y=CH$_2$, OH at 2-position] can be prepared by lithium aluminum hydride reduction of ethyl 2-(2-hydroxyphenylamino)benzoate according to the procedure of Example 1, part (b).

EXAMPLE 11

(a) 2-(4-Hydroxy-2-methylphenylamino)benzoic acid [XI; R=H, R''=2-CH$_3$, OH at 4-position], m.p. 209°–211° C. (decompn.) was prepared by boron tribromide demethylation of 2-(4-methoxy-2-methylphenylamino)benzoic acid, in turn prepared by reaction of 2-chlorobenzoic acid with 2-methyl-4-methoxyaniline.

(b) It is contemplated that 2-(4-hydroxy-2-methylphenylamino)benzenemethanol [I; R and R'=H, R''=2-CH$_3$, Y=CH$_2$, OH at 4-position] can be prepared by lithium aluminum hydride reduction of 2-(4-hydroxy-2-methylphenylamino)benzoic acid according to the procedure of Example 1, part (b).

The compounds of Formulas I and II have been found to inhibit lipoxygenase activity in biological systems, thus indicating their usefulness as anti-asthmatic agents.

Slow reacting substance of anaphylaxis (SRA-A) is a descriptive term for a family of lipoxygenase metabolic products of arachidonic acid designated as the leukotrienes. These substances are potent contractile agents of vascular and pulmonary smooth muscle. The relationship of SRS-A to asthma was first characterized by Brockelhurst (rev. in Adv. Drug Res. 19, 109 (1970) who identified the material as being present subsequent to specific antigen challenge of living tissue obtained from asthmatic patients. Herxheimer and Stressmann (J. Physiol. 165, 78P (1953)) first demonstrated that aerosolized guinea pig SRS-A induced bronchospasm in man. This observation has been more recently confirmed using purified leukotrienes.

Recent studies have indicated that lipoxygenase inhibiting compounds may have therapeutic potential in treating diseased states other than asthma, e.g. bronchitis, acute inflammation, arthritis, psoriasis, cardiovascular insufficiency and myocardial infarct.

The primary screening test used is a determination of the inhibition of lipoxygenase and cyclooxygenase derived from rat basophilic leukemia (RBL-1) cells. The test was carried out according to the following procedure:

Single cell suspensions of RBL-1 cells are homogenized to obtain the microsomal fraction containing lipoxygenase and cyclooxygenase. Test compounds are added to the enzyme-containing homogenate for a 5 min preincubation period at 37° C. prior to the addition of $^{14}$C-arachidonic acid substrate. Following incubation at 37° C. for 15 min, the reaction is stopped by the addition of 2M formic acid and the enzyme-substrate products are extracted into chloroform. An aliquot of the extract is evaporated to dryness, reconstituted in ether to 1/10 original volume, spotted on thin layer chromatography plates and chromatographed. The peak areas of radioactivity representing the products are located by scanning the plates. The quantity of products formed is estimated by measuring the height of the radioactivity peaks observed on the chromatographic scans. Alternatively, the areas of radioactivity are scraped from the plate and the $^{14}$C quantitated by scintillation counting. The percent inhibition in the formation of the cyclooxygenase product PGD2, designated as Cl and lipoxygenase products, L1 designated for 5,12-di-HETE and L2 for 5-HETE are shown. Compounds with >50% inhibition of L1 and L2 at a screening concentration of 1 $\mu$M are considered active.

The compounds were tested in vivo by the effect on the SRS-A component of immunologically induced broncho-construction in guinea pigs. The test was carried out according to the following procedure:

Two weeks after immunization with egg albumin, guinea pigs are prepared for bronchoconstruction determination. One hour prior to antigen challenge, each animal is dosed orally with idomethacin and chlorpheniramine. Animals are anesthetized with sodium pentobarbital, the trachea cannulated and the animal artificially respired. Arachidonic acid is administered intravenously prior to antigen challenge. The resulting bronchoconstruction is recorded by the standard lung overflow procedure and the peak increase in intratracheal pressure (mm Hg) over a 10 minute observation period is recorded. Compounds are evaluated for their ability to prevent the increased intratracheal pressure in an experimental group of animals as compared to the medicated (indomethacin+chlorpheniramine+arachidonic acid) control group. The results are expressed in terms of percent inhibition or as ED$_{50}$ values (effective does in 50% of the animals).

| Example No. | In vitro % Inhibition[a] | IC$_{50}$[b] | In vivo Guinea Pig |
|---|---|---|---|
| 1c | C1 2 | >1 | ED$_{50}$ i.v. = |
| | L1 88 | 0.20 | 0.13 mg/kg |
| | L2 98 | 0.09 | |
| 2c | C1 4 | >1 | ED$_{50}$ i.v. = |
| | L1 84 | 0.38 | 0.84 mg/kg |
| | L2 94 | 0.28 | |
| 3c | C1 6 | >1 | ED$_{50}$ i.v. = |
| | L1 81 | 0.06 | 0.49 mg/kg |
| | L2 99 | 0.04 | |
| 4c | C1 24 | >1 | 63% at 1–3 mg/kg, i.v. |
| | L1 82 | 0.23 | 43% at 0.3 mg/kg, i.v. |
| | L2 100 | 0.16 | |
| 5c | C1 14 | >1 | |
| | L1 86 | 0.2 | |
| | L2 99 | 0.18 | |
| 6c | C1 2 | >1 | |
| | L1 89 | 0.2 | |
| | L2 98 | 0.16 | |
| 8 | C1 0 | >1 | ED$_{50}$ i.v. = |
| | L1 85 | 0.19 | 0.12 mg/kg |
| | L2 96 | 0.15 | |

[a]Percent inhibition of cyclooxygenase (C1) and lipoxygenase (L1 and L2) formation at a dose of 1 μM.
[b]Inhibitory concentration (μM) in 50% of tests.

The benzyl ethers of Formula III were also tested for lipoxygenase inhibitory activity in vitro and found to possess a low degree of activity, very substantially less than that of the corresponding phenolic compounds of Formula I.

The compounds of the invention can be prepared for use by conventional pharmaceutical procedures: that is, by dissolving or suspending them in a pharmaceutically acceptable vehicle. e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

We claim:

1. A compound of the formula

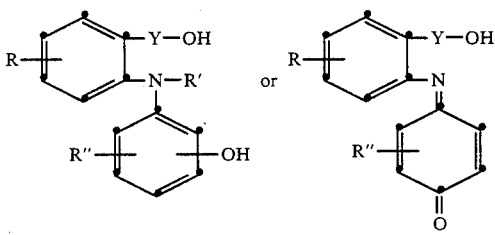

wherein:
R is hydrogen, lower-alkyl, lower-alkoxy or halo;
R' is hydrogen or lower-alkyl;
R" is hydrogen, lower-alkyl or halo; and
Y is C$_n$H$_{2n}$ wherein n is an integer from 1 to 2.

2. A compound according to claim 1 of the formula

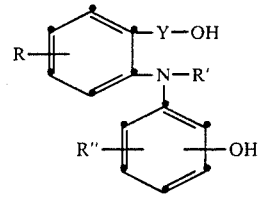

3. 2-(4-Hydroxyphenylamino)-5-methoxybenzenemethanol, according to claim 2.
4. 2-(4-Hydroxyphenylamino)benzenemethanol, according to claim 2.
5. 5-Chloro-2-(4-hydroxyphenylamino)benzenemethanol, according to claim 2.
6. 4-Chloro-2-(4-hydroxyphenylamino)benzenemethanol, according to claim 2.
7. 2-(4-Hydroxyphenylamino)-α-methylbenzenemethanol, according to claim 2.
8. 2-(4-Hydroxyphenylamino)-5-methoxy-α-methylbenzenemethanol, according to claim 2.
9. 2-(3-Chloro-4-hydroxyphenylamino)benzenemethanol, according to claim 2.
10. A compound according to claim 1 of the formula

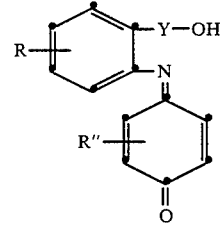

11. 4-(2-Hydroxymethyl-4-methoxyphenylimino)-2,5-cyclohexadien-1-one, according to claim 10.
12. A compound of the formula

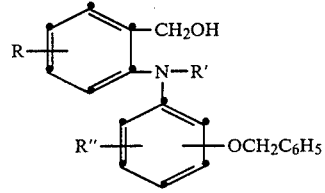

wherein:
R is hydrogen, lower-alkyl, lower-alkoxy or halo;
R' is hydrogen or lower-alkyl; and
R" is hydrogen, lower-alkyl or halo.
13. 2-(4-Benzyloxyphenylamino)-5-methoxybenzenemethanol, according to claim 12.
14. 2-(4-Benzyloxyphenylamino)benzenemethanol, according to claim 12.
15. 5-Chloro-2-(4-benzyloxyphenylamino)benzenemethanol, according to claim 12.
16. 2-[Methyl(4-benzyloxyphenyl)amino]benzenemethanol, according to claim 12.
17. A composition for the treatment or prevention of allergic asthma which comprises an anti-asthmatically effective amount of a compound according to claim 1 together with one or more pharmaceutically acceptable excipients or diluents.
18. A composition according to claim 17 wherein the anti-asthmatically effective compound is 2-[(4-hydroxyphenyl)amino]-5-methoxybenzenemethanol.
19. A method for treating or preventing allergic asthma in a mammal which comprises administering to said mammal a composition according to claim 17.
20. A method according to claim 19 in which the anti-asthmatically effective compound is 2-[(4-hydroxyphenyl)amino]-5-methoxybenzenemethanol.

* * * * *

UNITED STATES PATENT AND TRADEMARK OFFICE
CERTIFICATE OF CORRECTION

PATENT NO. : 4,496,590

DATED : January 29, 1985

INVENTOR(S) : Donald C. Schlegel and Malcolm R. Bell

It is certified that error appears in the above-identified patent and that said Letters Patent is hereby corrected as shown below:

Column 5, line 65, "halid" should read --halide--.

Column 6, line 36, delete "in", second occurrence; line 66, "282 g" should read --284 g--.

Column 9, line 44, "Benzyloxphenylamino" should read --Benzyloxyphenylamino--.

Column 11, line 62, "(SRA-A)" should read --(SRS-A)--; line 68, "rev." should read --Rev.--.

Column 12, lines 47, 51 and 57-8, "bronchoconstruction", each occurrence, should read --bronchoconstriction--.

UNITED STATES PATENT AND TRADEMARK OFFICE
CERTIFICATE OF CORRECTION

PATENT NO. : 4,496,590
DATED : January 29, 1985
INVENTOR(S) : Donald C. Schlegel and Malcolm R. Bell It is certified that error appears in the above-identified patent and that said Letters Patent is hereby corrected as shown below:

Column 12, line 53, "idomethacin" should read --indomethacin--; line 67, "does" should read --dose--.

Column 13, insert as a paragraph before line 1:

--The following Table summarizes the results obtained from the testing of the compounds of Formulas I and II.--

Signed and Sealed this

Twenty-eighth Day of May 1985

[SEAL]

Attest:

DONALD J. QUIGG

Attesting Officer     Acting Commissioner of Patents and Trademarks